(12) United States Patent
Baniel

(10) Patent No.: US 6,627,768 B1
(45) Date of Patent: Sep. 30, 2003

(54) PROCESS FOR RECOVERY OF ACID

(75) Inventor: Avraham Baniel, Jerusalem (IL)

(73) Assignee: A. E. Staley Manufacturing Company, Decatur, IL (US)

( * ) Notice: Subject to any disclaimer, the term of this patent is extended or adjusted under 35 U.S.C. 154(b) by 0 days.

(21) Appl. No.: 10/089,029

(22) PCT Filed: Sep. 17, 2000

(86) PCT No.: PCT/IL00/00573
§ 371 (c)(1),
(2), (4) Date: Mar. 26, 2002

(87) PCT Pub. No.: WO01/27063
PCT Pub. Date: Apr. 19, 2001

(30) Foreign Application Priority Data

Oct. 8, 1999 (IL) .................................................. 132289

(51) Int. Cl.[7] .......................... C07C 69/66; C07C 69/34; C07C 69/52; C07C 67/48; C07C 51/42
(52) U.S. Cl. ........................ 560/179; 560/180; 560/190; 560/191; 562/580; 562/589; 562/593; 562/606; 562/608
(58) Field of Search ................................. 562/580, 589, 562/593, 606, 608, 582, 584; 560/179, 180, 190, 191

(56) References Cited

U.S. PATENT DOCUMENTS

| 4,275,234 A | 6/1981 | Baniel et al. ................ 562/584 |
| 5,750,732 A | 5/1998 | Verser et al. ................ 549/274 |
| 5,892,109 A | 4/1999 | Baniel et al. ................ 562/580 |

Primary Examiner—Mukund J. Shah
Assistant Examiner—Zachary C. Tucker
(74) Attorney, Agent, or Firm—Williams, Morgan & Amerson, P.C.

(57) ABSTRACT

The invention provides a process for the conversion of an extracted carboxylic acid to a non-ionized derivative thereof, comprising contacting a carboxylic acid containing aqueous solution with a water-insoluble amine solvent, to recover acid therefrom and to form an extract carrying amine-bound carboxylic acid, characterized in that said extract is contacted with a concentrated aqueous solution of said same acid of high concentration, whereby additional acid is transferred to said extract to form a loaded extract and said loaded extract is reacted to form a non-ionized derivative of said acid, by reactions known per se, whereby said acid is converted into a non-ionised derivative form and said amine solvent is liberated for recycling.

7 Claims, 1 Drawing Sheet

PROCESS FOR RECOVERY OF ACID

Figure 1:
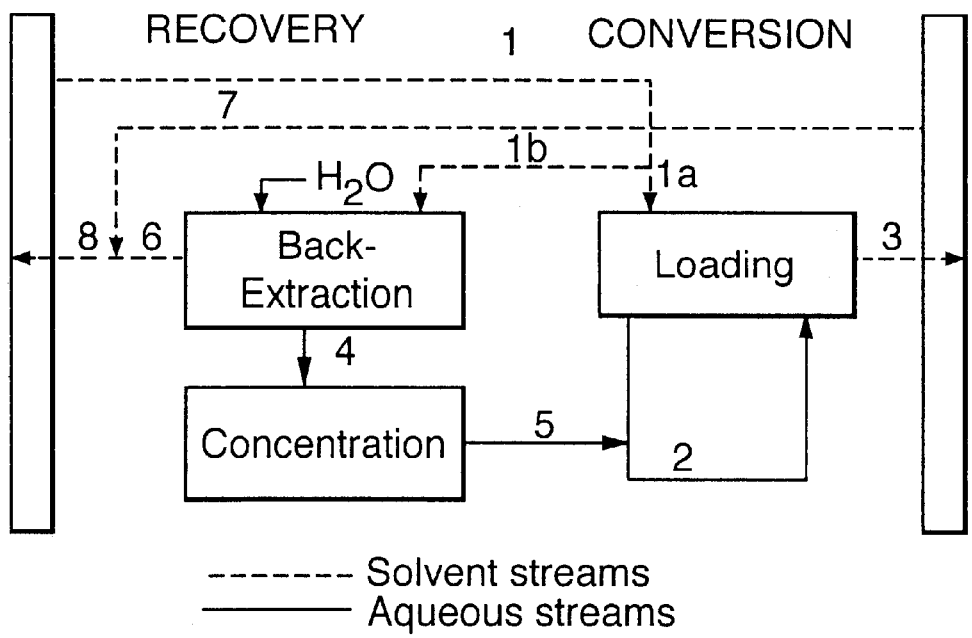

This application was filed under 35 U.S.C. 371, and is the U.S. National Phase of PCT/DL00/00573 filed Jan. 19, 2000.

The present invention relates to the fields of recovery of acids, in particular carboxylic acids, by means of amine extractants and of conversion of the recovered acids to derivatives. More particularly, the present invention relates to a process for the conversion of an extracted carboxylic acid to a non-ionized derivative thereof.

In the most general case these fields of recovery of acids by means of amine extractants and of conversion of the recovered acids to non-ionized derivatives—which fields, and techniques thereof, are known per se—provide for a sequence of two independent processes: the first for the recovery of an acid (as a crystalline product or an aqueous solution), and the second for the conversion of such recovered acid into a desired derivative such as salt, ester, polyacid etc.

These two fields, however, may be combined with benefit in cases in which the acid can be converted while still carried by a water-insoluble amine solvent, hereinafter referred to as the "extract"—and the acid conversion product recovered directly. Thus an extract of an acid that forms water-soluble salts can be reacted with an aqueous alkali in a single contact to form an aqueous salt solution and concurrently releasing the amine solvent (hereinafter referred to as the "extractant"). By such procedure the "back-extraction" operation of the acid recovery process, in which the acid is back-extracted by water, is eliminated.

U.S. Pat. No. 4,275,234 to Baniel et al. is illustrative of recovering carboxylic acids, as such, by means of extraction and back-extraction with an amine solvent. Similarily, U.S. Pat. No. 5,231,225 to Baniel et al. illustrates recovery by alkali. These examples are not unique. They fall within an extensive published prior art.

In analogy of converting acids to salts, directly in the extract, one could seek direct conversion to other derivatives. Indeed established chemistry provides for converting amine-bound acids to typical derivatives such as esters. This is particularly true of carboxylic acids which bond weakly to amines, such as trialkylamines of 20 C-atoms or higher typically used in Solvent Extraction. Thus citric acid can be converted to the ethyl ester, lactic acid can be converted variously to the ethyl ester, to polylactic acid and to lactide. A weak amine, similarly to hydrocarbons and other neutral solvents, is essentially inert with respect to such reactions. The term "neutral" as used herein is intended to denote that the solvent does not take part in the reaction itself though it may be assisting it directly or indirectly.

In order to illustrate the applicability of reactions in the presence of solvents that are neutral, the case of conversion of lactic acid to a variety of its non-ionized derivatives is considered.

U.S. Pat. Nos. 5,420,304 and 5,750,732, both to Verser et al. both teach processes for making cyclic esters of hydroxyacids inclusive of lactide and polylactic acids from lactic acid in the presence of a great variety of neutral solvents. Such conversions have been known for many years to take place in the absence of solvents e.g. Carothers et al. and others quoted in the same patent. The solvents are thus obviously neutral in the sense given above to this word. The reasons for their use may be connected to reaction facilitation or to their presence due to having been used in the recovery of the carboxylic acid by Solvent Extraction. This last case, claimed by Verser et al., is of particular relevance to the present invention as explained in detail hereinafter.

U.S. Pat. No. 5,319,107 to Benecke et al. specifically describes "alkyl or aryl amine salts" (ibid page 5, lines 5–8) as preferred starting materials for making cyclic esters from hydroxy acids such as lactide from lactic acid. It should be noted that the term "amine salts" is an accepted way to describe the state of a carboxylic acid carried in an amine solvent phase such that is typically obtained by Solvent Extraction applying such an amine solvent.

EP 0 789 080 A2 to Kamm et al. titled: "Method for the preparation of organic ammonium lactates and their application in the production of dilactide" claims a particular class of amines for purposes broadly defined in the previous cited patent.

The foregoing brings out the desirability of converting carboxylic acids, in particular carboxylic acids obtained in a solvent phase extract in a solvent recovery process, to product derivatives, while still carried in the organic phase of the extract. In addition to possible savings in back-extraction and subsequent operations, the very fact that the extract is free of water or nearly so can be of considerable advantage in reactions that involve water elimination such as esterification, lactonisation etc. as brought out in the cited patents and the numerous references cited therein.

The extensive use of these attractive possibilities is constrained however by the divergence between the demands of acid recovery by extraction with the demands of converting the acid as obtained in the extract. Typically the extract will contain acid at a low concentration level whereas for conversion of the acid a high concentration is desirable.

The last point relates to the sharp difference that obtains in converting carboxylic acids carried in an amine solvent extract to inorganic water soluble salts and their conversion to non-ionised organic derivatives such as esters. In the former case the concentration of the salt is determined by the concentration of the alkali used to react with the acid; in the latter case the solvent acts as a diluent which tends generally to affect negatively equilibria, reaction rates and separation costs.

The purpose of the present invention is to provide for simple ways to remedy this divergence, as well as to provide means that are easily adaptable to currently used industrial procedures.

With this state of the art in mind, there is now provided according to the present invention a process for the conversion of an extracted carboxylic acid to a non-ionized derivative thereof, comprising contacting a carboxylic acid containing aqueous solution with a water-insoluble amine solvent, to recover acid therefrom and to form an extract carrying amine-bound carboxylic acid, characterized in that said extract is contacted with a concentrated aqueous solution of said same acid of high concentration, whereby additional acid is transferred to said extract to form a loaded extract and said loaded extract is reacted to form a non-ionized derivative of said acid, by reactions known per se, whereby said acid is converted into a non-ionised derivative form and said amine solvent is liberated for recycling.

In preferred embodiments of the present invention said amine-bound acid extract is split into two streams, a first stream of which is back-extracted with water and concentrated to form said concentrated solution for recombination with said second extract stream.

In the present invention said loaded extract, carrying amine-bound carboxylic acid, may be reacted to form a non-ionized derivative of said acid by intra-molecular or inter-molecular reactions of the acid or reactions of the acid with a reagent, all of which reactions are known per se and do not form a part of the present invention.

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Figure 2:
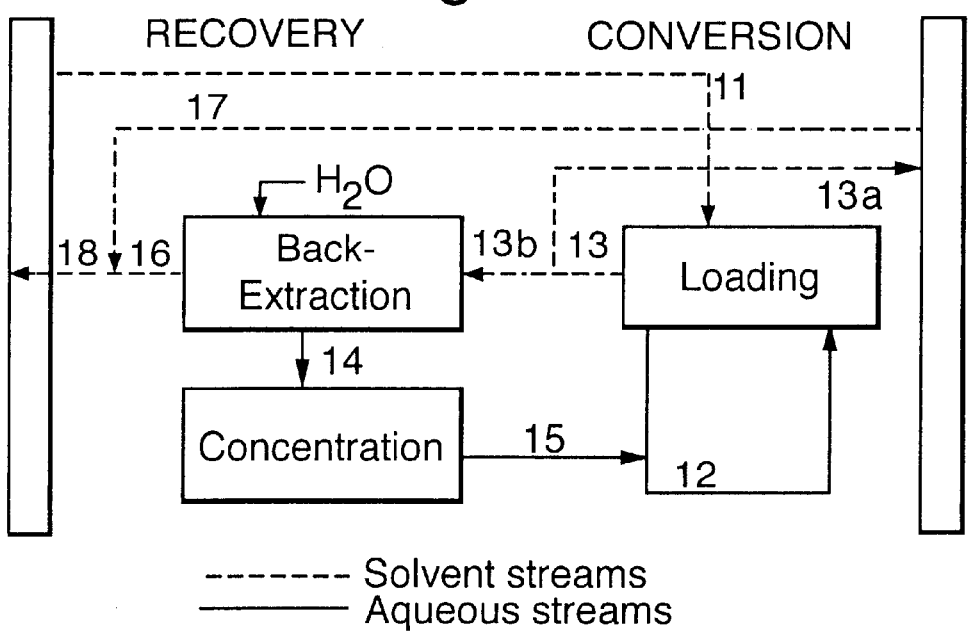

In the drawings:

FIG. 1 is a schematic flow diagram of a preferred process according to the present invention; and FIG. 2 is a schematic flow diagram of a variant process according to the present invention.

Referring now to FIG. 1:

"recovery" represents a process that results in an extractant (an amine solvent) carrying an acid—the extract.

"conversion" represents a process that consumes acid carried by the same extractant in which the acid is chemically converted and the extractant liberated.

(1) is an acid carrying extract stream produced in recovery which is split into two streams (1a) and (1b);

(1a) is contacted in loading with a concentrated aqueous solution of the same acid (2) of high concentration whereby (1a) is loaded with additional acid to provide an extractant stream (3) carrying acid at a desirably high level; since the concentration of (2) can be established at will as well as the ratio of (1a) brought into contact with (2)—a single contact will generally suffice to ensure the desired composition of (3);

(3) carries acid in amount approximately equal to that of (1) and is the feed to conversion in which the acid is converted to the desired product thereby liberating the extractant contained in it—(7) which is recycled to recovery.

(1b) is subjected to back-extraction with water whereby the acid it carries is transferred to an aqueous stream (4); the acid-free extractant (6) which forms concurrently rejoins (7) to form (8) which recycles the extractant to recovery;

(4) that contains acid in approximately equal amount to the increment by which (1a) was loaded to form (3) is concentrated, as necessary, so as to provide (5) as make-up to the loading solution (2).

A variant of the process is illustrated in FIG. 2.

In this case extractant stream (11) that carries the acid from recovery is not split prior to loading as in the previous variant. All of it is loaded to the desired level and the loaded stream (13) is split to (13a) that reports to conversion and (13b) that reports to back-extraction. All the rest is identical with the previous scheme, but stream (14) will be more concentrated than in the previous scheme. This results in lower demands on concentration and possibly with its complete elimination.

Both schemes are valid in all cases. However, depending on the characteristics of each particular case one or the other may be preferable. This can be generally derived from distribution graphs, if available, or established by a few simple experiments.

The following examples illustrate the foregoing modes of practicing the present invention. For clarity and by way of illustration, recovery where the extract originates and conversion where the acid carried by the extract is reacted are described in examples below but no claim is made thereby to these operations nor any limitation is implied with respect to the invention that, by itself, relates to changing the ratio of acid to amine solvent in the extract obtained in recovery for benefits realised in conversion.

EXAMPLE 1

100 grs of a filtered fermentation broth containing 16% citric acid by weight was extracted—according to the teaching of U.S. Pat. No. 4,275,234—at 33° C. by a solvent containing 1 mol of tridodecylamine and 5% n-octanol (the rest being hydrocarbons) at a weight ratio of 1.7:1 solvent:aqueous in five counter-current stages whereby 178 grs of extract were obtained containing virtually all of the citric acid. The extract contained close to 9% citric acid.

82 grs of the extract (corresponding to stream (1a) in FIG. 1) were contacted in 2 counter-current stages with 300 grs of an aqueous solution of 40% citric acid whereby 94 grs of a loaded extract of 17% citric acid was obtained and an aqueous phase in which the citric acid concentration was slightly lowered. The remainder of the extract of about 96 grs (corresponding to (1b) in FIG. 1) were back-extracted by 35 grs of water at 90° C. in 5 counter-current stages to obtain about 43 grs of an aqueous solution of 20% citric acid corresponding to stream (4) in FIG. 1. This solution was concentrated to about 42% to provide the make-up stream (5) of the loading solution (2).

The loaded organic stream (3) contained approximately 16 grs of citric acid, an amount equal to the citric acid contained in the solvent extract (1). This acid was reacted with ethylene oxide. This well known ethoxylation reaction converts citric acid to a water soluble compound recoverable by addition of water to the reaction mixture thereby liberating the water insoluble solvent (7) which was recycled to the process.

In a 9% extract the ratio of solvent to acid was close to 10; in the 17% loaded extract it was close to 5 i.e. the amount of solvent charged to conversion was cut by half.

EXAMPLE 2

This example illustrates the process variant represented by FIG. 2

178 grs of an extract identical with the extract of Example 1 representing stream (11) were contacted with 500 grs of an aqueous citric acid of 40% in a single stage whereby 198 grs of loaded extract stream (13) of citric acid concentration of 17%, as in the previous example, were obtained. 94 grs of this loaded extract representing (13a) were sent to conversion as in Example 1; the rest were back-extracted in 5 stages by 40 grs water at 90° C. and the citric acid recovered as 76 grs aqueous solution of over 42% representing make-up stream (15).

EXAMPLE 3

This example follows FIG. 1.

An extract (1)—obtained by extracting a lactic acid fermentation broth by a solvent of the same composition as in example 1—contained 3.2% lactic acid. 120 grs of this extract were split into 80 grs stream (1b) and 40 grs stream (1a). The latter was loaded by contact with lactic acid loading solution (2) of 30% lactic acid to obtain 44 grs of (3)

of 8.8% lactic acid and this lactic acid was converted to ethyl lactate by esterification with ethanol in the conversion section and the recovered solvent (7) returned to recovery. Stream (1b) was back-extracted with water at 85° C. and further concentrated to 32% lactic acid to provide make-up (5).

EXAMPLE 4

This example follows FIG. 2

An extract (11) composed of 52% tridodecylamine, 30% hydrocarbons, 12% normal propanol (nPrOH) and 6% lactic acid was loaded at room temperature by 3-stage counter-current contact with 32% aqueous lactic acid (12) to form a loaded extract (13) composed of of 57% tridodecylamine, 33% hydrocarbons and 10% lactic acid. This loading operation was done using 200 grs of the aqueous stream (12) to 100 grs of the extract (11). The nPrOH content of the organic extract (11) was extracted into the aqueous phase exiting loading and was recovered by distillation (not shown in FIG. 2) prior to rejoining (12). The distilled nPrOH was sent to extractant reconstitution in recovery. (13b) was back-extracted at 90° C. to form (14) of over 26% lactic acid the concentration of which was further adjusted by to form make-up (15). The lactic acid in (13a) was converted to lactide which separates from the solvent by virtue of its volatility and the released solvent (17) returned to recovery.

This example combines the advantage of providing a higher concentration of acid to conversion with the added advantage of eliminating the nPrOH which is detrimental to conversion though an essential enhancer of the extraction that takes place in recovery.

EXAMPLE 5

The procedure of example 4 is followed except that conversion results in polylactic acid that separates from the amine solvent by virtue of insolubility.

The last two examples show that the scheme of FIG. 2 is particularly well adapted to cases wherein the extractant used in recovery contains a recyclable "extraction enhancer" as described in U.S. Pat. No. 5,780,276 to Baniel, an invention which relates specifically to carboxylic acids and comprises an operation of "extraction of extractant solution with acidic RCOOH solution" shown as (B) in FIG. 1 therein. This operation which is an essential part of the practice of the invention of U.S. Pat. No. 5,780,276 can be thus adjusted to act also as the loading in FIG. 2 of the present invention.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the conversion of an extracted carboxylic acid to a non-ionized derivative thereof, comprising contacting a carboxylic acid containing aqueous solution with a water-insoluble amine solvent, to recover acid therefrom and to form an extract carrying amine-bound carboxylic acid, characterized in that said extract is contacted with a concentrated aqueous solution of said same acid of high concentration, wherein said extract, carrying amine-bound carboxylic acid, is split into two streams, a first stream which is back-extracted with water and concentrated to form said concentrated solution for contact with said second stream, whereby additional acid is transferred to said extract to form a loaded extract and said loaded extract is reacted to form a non-ionized derivative of said acid, by reactions known per se, whereby said acid is converted into a non-ionized derivative form and said amine solvent is liberated for recycling.

2. A process according to claim 1, wherein said loaded extract, carrying amine-bound carboxylic acid, is reacted with a reagent.

3. A process according to claim 2, wherein said reagent is an alcohol and said non-ionized derivative is an ester.

4. A process according to claim 1, wherein lactic acid carried by a loaded extract is reacted to form lactide as the non-ionized derivative.

5. A process according to claim 1, wherein lactic acid carried by a loaded extract is reacted to form polylactic acid as the non-ionized derivative.

6. A process according to claim 1, wherein said non-ionized derivative is formed by intra-molecular reactions of the acid carried by said loaded extract.

7. A process according to claim 1, wherein said non-ionized derivative is formed by inter-molecular reactions of the acid carried by said loaded extract.

* * * * *

UNITED STATES PATENT AND TRADEMARK OFFICE
CERTIFICATE OF CORRECTION

PATENT NO.   : 6,627,768 B1
DATED        : September 30, 2003
INVENTOR(S)  : Avraham Baniel It is certified that error appears in the above-identified patent and that said Letters Patent is hereby corrected as shown below:

Column 6,
Line 22, insert -- of -- between "stream" and "which".
Line 35, insert -- is -- after "acid".

Signed and Sealed this

Eighteenth Day of November, 2003

JAMES E. ROGAN
*Director of the United States Patent and Trademark Office*